United States Patent [19]

Hardesty et al.

[11] Patent Number: 5,358,862
[45] Date of Patent: Oct. 25, 1994

[54] SYNTHETIC TRNAS

[75] Inventors: Boyd Hardesty; Wendy L. Picking, both of Austin, Tex.

[73] Assignee: Research Development Foundation, Carson City, Nev.

[21] Appl. No.: 914,212

[22] Filed: Jul. 14, 1992

Related U.S. Application Data

[62] Division of Ser. No. 753,266, Aug. 30, 1991, abandoned.

[51] Int. Cl.$^5$ .................... C12N 15/11; C07H 21/04
[52] U.S. Cl. ................. 435/172.3; 536/23.1; 935/3; 935/17
[58] Field of Search .............. 435/172.3; 536/27; 935/3, 17

[56] References Cited

PUBLICATIONS

Schulman (1991) Progress in Nucleic Acid Research and Molecular Biology 2:23–87.
Normanly et al., (1989) Annual Review of Biochemistry 58:1029–49.
Bull et al., (1987) DNA 6:353–362.
Bruce et al., (1982) Biochemistry 21:3921–3926.
Gavini et al., (1992) J. Biological Chemistry 266:2240–2243.
E. Katchalski et al., "Synthesis & Chemical Properties of poly-α-amino acids"in Advances in Protein Chemistry 13 (1958) pp. 243–292.

*Primary Examiner*—Robert A. Wax
*Assistant Examiner*—Gabriele Bugaisky
*Attorney, Agent, or Firm*—Fulbright & Jaworski

[57] ABSTRACT

Synthetic tRNAs are produced from tRNA$^{Cys}$(AAA), tRNA$^{Ser}$(AAA), tRNA$_e^{Ala}$(AAA), and tRNA$_f^{Ala}$(AAA) genes. Polyuridylic acid-dependent syntheses of polypeptides were carried out in vitro on *E. coli* ribosomes using the synthetic tRNAs.

12 Claims, 5 Drawing Sheets

FIG. 1C

```
                                          GGC
HIII T7 promoter
AGCTTTAATACGACTCACTATAGGGCTATAGCTCAGCTGGGAGAGCGCCTGCTTAAAACGCAGGAGGTC
                                                   BstNI/BamHI
TGCGGTTCGATCCCGCGTAGCTCCACCAGGATCC
```

FIG. 1D

```
                            C C              *              C T
HIII T7 promoter
AGCTTTAATACGACTCACTATAGGGGGGTGGAGCAGCCATGGTAGCTCGTCGGGCTAAAAACCCGAAGG
                            G A                         BstNI/BamHI
TCGTCGGTTCAAATCCGGCCCCCCTCTACCAGGATCC
```

SYNTHETIC TRNAS

This application is a division of application Ser. No. 07/753,266 filed Aug. 30, 1991, now abandoned.

BACKGROUND OF THE INVENTION

This invention relates generally to the in vitro synthesis of peptides and, more particularly, to the synthesis of nascent peptides on *Escherichia coli* ribosomes using synthetic tRNA species.

Scientists have for a long time been trying to develop a methodology that will make it possible to efficiently modify and produce proteins outside living cells. One technical component of this endeavor is the modification of tRNAs with altered anticodon or recognition sites for enzymatic aminoacylation. The modified tRNAs make it relatively simple to substitute different amino acids at a target site of a protein by generating a single new codon which can be read by each of a series of modified tRNAs.

By using a series of modified tRNAs, one each for a different amino acid, the specific amino acid can be incorporated into the protein at the target site(s) of interest. Since under most circumstances only one protein is synthesized in any system, the effect of the amino acid substitution on the activity of the polypeptide can be measured directly without producing a clone for each amino acid substitution and without the problems frequently associated with expression and subsequent testing of a protein produced in intact cells.

Ultimately, as the ability to predict the tertiary structure of a protein from its amino acid sequence is refined, it will be possible to produce totally designed proteins using mRNA that contain only 20 codons, one for each of the 20 naturally occurring amino acids for which there is a codon in the universal genetic code. Amino acids also can be incorporated into one or more specific sites in the protein by using modified tRNAs containing anticodons for some of the unused 41 codons. Further, by using chemical, rather than enzymatic aminoacylation of the modified tRNAs, it will be possible to incorporate amino acids that have no naturally occurring counterpart into these "artificial proteins." This will make it possible to design, test, and produce artificial enzymes that use catalytic mechanisms and substrates that do not occur in living organisms.

The acylation of tRNA with a specific amino acid may be carried out by either chemical or enzymatic reactions, the latter using aminoacyl-tRNA synthetases (AS). Procedures for chemical aminoacylation of tRNAs are known. S. A. Robertson et al. (1989) *Nucl. Acid Res.* 17:9649–9660; M. Hagen et al. (1988) *J. Org. Chem.* 53:5040–5045.

In living systems, an AS must recognize with high specificity both the amino acid and the tRNA to be aminoacylated. Recognition of a tRNA species by the AS depends on specific structural features in the tRNA. There is no one single set of structural features in different tRNAs that specify their recognition by their cognate AS. C. de Duve (1988) *Nature* 333:117–118. Many of the structural features for tRNA identity appear not to be strictly conserved for a specific tRNA species in different organisms. Considerable variation in the specificity for aminoacylation of synthetic tRANs has been found with ASs from *E. coli*, yeast and rabbit reticulocytes and for conditions (salt and spermine or spermidine concentration, temperature) under which aminoacylation is carried out. Some principles for tRNA recognition by cognate AS have emerged. Some AS appear to have strict requirements for all of the anticodon, while others recognize only part of the anticodon. Met-tRNA AS appear to be highly dependent on the CAU anticodon (G. Ghosh et al. (1990) *Biochem.* 29:2220–2225); ASs for other tRNAs may require the second or third nucleotide of the anticodon.

ASs for other amino acids appear to recognize features of tRNA that are independent of the anticodon, but respond to positive, and in some cases negative, recognition sites elsewhere in the tRNA structure. The result of Schimmel and Hou demonstrate that G3-C70 base pair in the amino acid stem of tRNA$^{Ala}$ is the primary recognition cite for the AlatRNA AS. Y. M. Hou et al. (1988) *Nature* 333:140–145.

It is now potentially possible to design and produce synthetic tRNAs in vitro that are enzymatically aminoacylated and can be used in cell-free translation systems. These synthetic tRNAs may be of considerable value in elucidating ribosome function particularly with respect to movement of the nascent peptide within the ribosome and its folding into an active confirmation. The precise position and confirmation of nascent peptide as they are formed in ribosomes remain unknown.

SUMMARY OF THE INVENTION

It is therefore an object of the invention to provide synthetic tRNAs.

Another object of the invention is to provide methods of producing the synthetic tRNAs.

A further object of the invention is to provide enhanced polypeptides in vitro using the synthetic tRNAs.

According to the present invention the tRNA$^{Cys}$, tRNA$^{ser}$, tRNA$_e$$^{Ala}$ and tRNA$_f$$^{Ala}$ are encoded by the DNA sequences shown in FIG. 1A–D.

BRIEF DESCRIPTION OF THE DRAWINGS

The features of this invention which are believed to be novel are set forth with particularity in the appended claims. The invention itself, however, together with its objects and advantages thereof, will best be understood by reference to the following description taken in connection with the accompanying drawings, in which:

FIG. 1A–1D shows the sequences for pCYS, pSER, pALA and pFMET. The sequences for tRNA$^{Cys}$(GCA) and tRNA$^{Ser}$(GGA) are from M. Sprinzl et al. (1984) *Nucl. Acid Res.* 12:r1–r131. Positions of restriction sites and the 17 base T7 RNA polymerase promoter are indicated. The letters shown above each sequence represent nucleotides in the wild-type sequence which have been replaced. For each tRNA, the AAA anticodon is underlined. 1A: the tRNA$^{Cys}$(AAA) gene (pCYS or SEQ. ID. NO. 1) was constructed from four synthetic oligomers which were annealed and ligated into HindIII/BamHI-digested pUC18. The four oligomers are shown with solid lines above and below the pCYS sequence. The star above the pCYS sequence indicates where a base has been inserted. 1B: the tRNA$^{Ser}$(AAA) gene (pSER or SEQ. ID. NO. 2) was constructed by copying the tRNA$^{Ser}$(GGA) gene from the *E. coli* genome by PCR using two specific primers. These primers are shown by solid lines above and below the pSER sequence. In pSER, the T to A substitution was made to increase aminoacylation. 1C: the tRNA$_e$$^{Ala}$(AAA) gene (pALA or SEQ. ID. NO. 3) was constructed by copying the tRNA$^{Ala}$(GGC) gene from the *E. coli* genome by PCR. 1D: the tRNA$_f^{Ala}$(AAA) gene (pFMET or SEQ. ID. NO. 4) was constructed by copying the tRNA$_f^{Met}$(CAT) gene from the E. coli genome by PCR. The star above the pFMET sequence indicates where a base has been inserted.

FIG. 3A shows synthesis initiated with CPM-Phe-tRNA and FIG. 3B shows synthesis initiated with CPM-Ser-tRNa. AcPhe-tRNA (0.5 μM) was prebound to poly(U)-programmed ribosomes (0.5 μM) to facilitate the synthesis of polyalanine with either 0.3 A$_{260}$ of tRNA$_f^{Ala}$(AAA) (open symbols) or 0.1 A$_{260}$ tRNA$_e^{Ala}$(AAA) (closed symbols) as the elongator tRNA source in a final volume of 0.1 ml. [$^{14}$C]Alanine incorporation was measured after incubation at 37° C. for the times indicated by deacylating all the aminoacylated tRNA with 0.5 M NaOH, then precipitating polyalanine with 5 ml ice cold 10% trichloroacetic acid and determining the radioactivity of the precipitate. Polyalanine synthesis in the presence of 4 μM erythromycin was also measured for comparative purposes ( - - - ).

FIG. 4A measurements were in a final volume of 600 μl for the free (—) and ribosome-bound ( - - - ) tRNAs. Ribosomes were present at 0.5 μM. After the ribosomes were added, the reaction mixtures were incubated for 15 min at 37° C. Fluorescence measurements were carried out at 20° C. with an excitation wavelength of 385 nm. After the measurements were complete, erythromycin was added to a final concentration of 4 μM and the effect of erythromycin binding on the spectrum of each ribosome-bound tRNA was monitored (    ).

DESCRIPTION OF THE PREFERRED EMBODIMENT

Figure 1A:
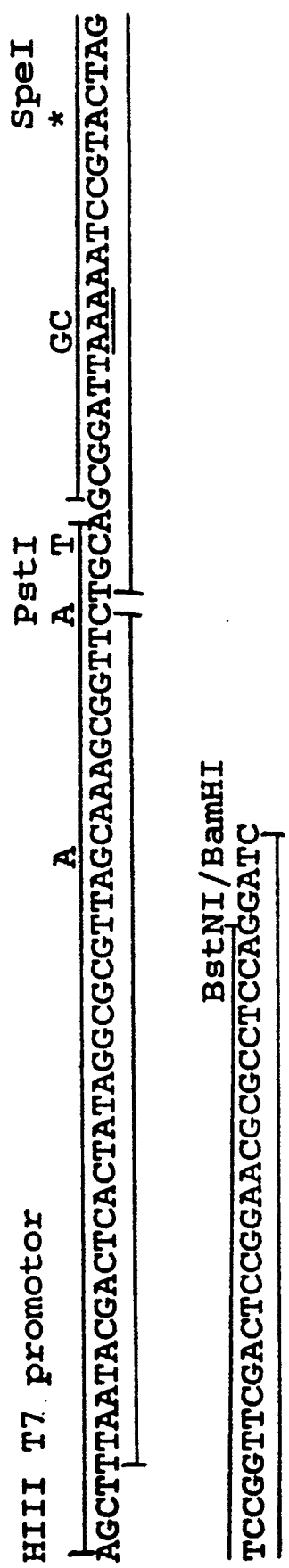

The conformation of the nascent peptide as it is extended out of the ribosome is likely to be critical in determining how the final peptide product is folded. Compelling evidence has been reported that some, perhaps all, nascent peptides produced from natural mRNAs exit the ribosome on the outer surface of the large ribosomal subunit at a point distal to the peptidyl transferase center. C. Bernaeu et al. (1980) Proc. Natl. Acad. Sci. USA 79:3111–3115. A portion of nascent peptides containing 30 to 40 amino acids is protected from protcolysis by the ribosome. L. I. Makin et al. (1967) J. Mol. Biol. 26:329–346. This may reflect the length of peptide required to span the distance between the peptidyl transferase center and the exit domain.

The conformation of the natural nascent peptides as they leave the peptidyl transferase center are unknown. W. D. Picking et al. ((1990) J. Biol. Chem. 266: 1534–1542) have demonstrated that elongating nascent phenylalanine and lysine behave quite differently as they are formed with poly(U) and poly(A), respectively. In an attempt to understand these findings, synthetic tRNA species which promote the poly(U)-directed synthesis of polypeptides were created.

Materials and Chemicals

The following abbreviations are used in this application and defined here: EDTA, ethylenediamine tetraacetic acid, disodium salt; HEPES, N-(2hydroxyl) piperazine-N'-2-ethanesulfonic acid; TRIS, tris-(hydroxymethyl)aminomethane; Poly(U), polyuridylic acid; Poly(A), polyadenylic acid; AcPhe-tRNA, Phe-tRNA which was acylated on its α-amino group; CPM-Phe-tRNA, Phe-tRNA which was mercaptoacetylated at its α-amino group and then reacted with CPM; CPM-Ser-tRNA, Ser-tRNA$^{Ser}$(AAA), which was mercaptoacetylated at its α-amino group and then reacted with CPM; CPM, 3(4-maleimidophenyl)-7-diethylamino-4methylcoumarin; tRNA$^{Cys}$(AAA), synthetic tRNA$^{Cys}$ which contains a AAA anticodon; tRNA$^{Ser}$(AAA), synthetic tRNA$^{Ser}$ which contains a AAA anticodon; tRNA$_e^{Ala}$(AAA), synthetic elongator tRNA which contains a AAA anticodon; tRNA$_f^{Ala}$(AAA), synthetic initiator tRNA which contains a AAA anticodon; LB, Lennox LB medium; X-gal, 5-bromo-4-chloro-3-indolyl-β-D-galactopyranoside; PCR, polymerase chain reaction.

Plasmid pUC18 was purchased from Bethesda Research Laboratories (Gaithersburg, Md.). Oligodeoxyribonucleotides were synthesized on an Applied Biosystems (Foster City, Calif.) 381A Synthesizer and purified on Applied Biosystems OPC columns according to manufacturer's specifications. The Klenow fragment of DNA polymerase, T4 DNA ligase, RNasin, and restriction endonucleases were obtained from Promega Biotec (Madison, Wis.). BstNI and BstBI restriction endonucleases were purchased from New England BioLabs (Beverly, Mass.). PCR reagents were from Perkin-Elmer Cetus (Norwalk, Conn.). Double-stranded sequencing was performed with the Sequenase II kit from United States Biochemicals (Cleveland, Ohio). [α-$^{35}$S]dATP, [$^{35}$S]cysteine, [$^{14}$C]phenylalanine, and [$^{14}$C]serine were purchased from New England Nuclear (Boston, Mass.). Deoxy- and ribonucleotides and guanosine monophosphate were obtained from Pharmacia (Piscataway, N.J.). CPM was from Molecular Probes (Junction City, Oreg.). Yeast tRNA$^{Phe}$ was from Sigma Chemical Co. (St. Louis, Mo.). Purified E. coli initiation factor 2 (IF-2) was a generous gift from Dr. C. Gualerzi (Max-Planck-Institut fur Molekulare Genetik, Berlin). NuSieve GTG agarose was from FMC (Rockland, Me.). Spectra-Gel A202 was purchased from Fisher Scientific (Houston, Tex.). T7 RNA polymerase was isolated from E. coli BL21 harboring the plasmid pAR1219 and purified according to the procedure of P. Davanloo et al. (1984) Proc. Natl. Acad. Sci. USA, 949:71–78. E. coli K12, strain A19, was originally provided to us by Drs. K. Nierhaus and H. G. Wittmann, Berlin. The growth and maintenance of these organisms and the isolation of ribosomal subunits has been described by O. Odom et al. (1980) *Biochemistry* 19:5947–5954.

Construction of pCYS

A synthetic tRNA to be aminoacylated with cysteine was chosen for synthesis because of the ease and specificity with which cysteine-sulfhydryl groups can be reacted with maleimide or alkylhalide derivatives of fluorophores. Previous studies have shown that the Cys-tRNA synthetase recognizes the 3:70 base pair of the tRNA acceptor stem and not the base composition of the anticodon. Y. M. Hou et al. (1988) *Nature* 33:140–145. Thus, one can form a Cys-tRNA that would recognize poly(U) in the cell-free translation system.

The tRNA$^{Cys}$(AAA) gene (pCYS or SEQ. ID. NO. 1) containing a HindIII site, T7 RNA polymerase promoter, mutant E. coli gene, BstNI site and BamHI site was synthesized as shown in FIG. 1A. In order to maintain as much similarity to wild-type tRNA$^{Cys}$ as possible, only three sites were altered in its base sequence. First, the anticodon was changed from ACA to AAA. Then, to allow for transformant screening and future genetic manipulation, two internal restriction sites were created. A PstI site was created in the D stem by changing bases A21 and T24 to C21 and C24, respectively. In order to maintain base pairing in the stem, A10 was changed to G10. An SpeI site was created in the extra arm by adding an A between U42 and C43.

In separate reactions, the 5'-3', and 3'-5' HindIII/PstI oligomers and the 5'-3' and 3'-5' PstI/BamHI oligomers were annealed by heating to 65° C. and slowly cooling to 25° C. The two resulting double-stranded oligomers were ligated and inserted into HindIII/BamHI-digested pUC18 by incubating the three fragments overnight at 16° C. with T4 DNA ligase. E. coli XL1B was transformed with the ligation mixture and spread onto LB agar plates containing ampicillin and X-gal. Transformants with plasmids containing an insert were screened for the presence of the complete tRNA$^{Cys}$(AAA) gene using SpeI restriction analysis of minilysate plasmid DNA. Both strands of the insert were then sequenced.

Construction of pSER

Figure 1B:
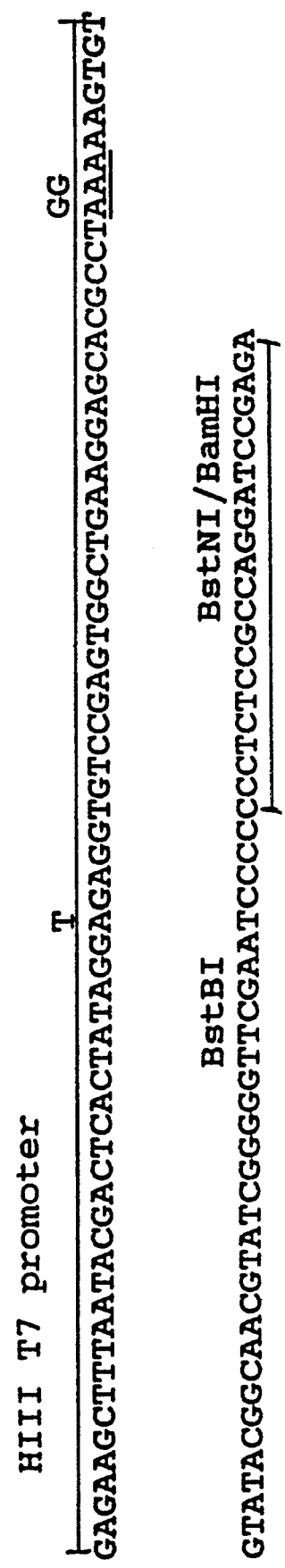

As is the case with the Cys-tRNA synthetase, Ser-tRNA synthetase recognizes portions of the tRNA other than the anticodon. J. Normanly and J. Abelson (1989) *Am. Rev. Biochem.* 58:1029–1049. Thus, a synthetic Ser-tRNA can be produced for utilization in the poly(U)-directed translation system. Rather than chemically synthesize the complete tRNA$^{Ser}$(AAA) gene sequence pSER or SEQ. ID. NO. 2), two oligomers were synthesized and used as PCR primers to copy the gene from the E. coli chromosome (FIG. 1B). The 5' primer contained four extra nucleotides at the 5' end, the 5'-3' HindIII sequence, the T7 RNA polymerase promoter, and 43 bases of the tRNA including the AAA anticodon. The 3' primer included four extra nucleotides, the 3'-5' BamIII and BstNI sequences and 12 bases of the tRNA. In contrast to the wild-type tRNA$^{Cys}$, a BstBI restriction site occurs within the T loop of tRNA$^{Ser}$, making a new restriction site for screening purposes unnecessary.

A 0.1 ml PCR reaction containing 100 pmol of each primer, 20 ng of E. coli chromosomal DNA, and 10 units of TaqI DNA polymerase, was overlaid with mineral oil and subjected to one cycle of 5 min at 94° C., 29 cycles of 1 min at 94° C., 2 min at 55° C., 3 min at 72° C., and one cycle of 1 min at 94° C., 2 min at 55° C., 10 min at 72° C. After cycling, the reaction mixture was extracted with chloroform and the products separated by electrophoresis on a 4% Nusieve GTG agarose gel using 40 mM Trisacetate (pH 7.8), 2 mM EDTA. The major product was the expected 124 bp fragment. After the agarose was removed by phenol-extraction, the ends of the 124 bp fragment were blunted using the Klenow fragment of DNA polymerase and digested with HindIII and BamHI. The fragment was then ligated into HindIII/BamHI-digested pUC18 by incubating overnight at 16° C. with T4 DNA ligase. E. coli XL1B transformants harboring a plasmid with an insert were screened for the presence of the complete tRNA$^{Ser}$(AAA) gene by BstBI restriction analysis using minilysate plasmid DNA. Both strands of the insert were sequenced.

Digestion of the pCYS and pSER by BstNI resulted in a linear transcriptional template having a single 5' overhanging thymidine that is complementary to the 3' terminal adenosine of the tRNA. Thus, runoff transcription of the BstNI digested pCYS or pSER would be expected to produce either a 75 or 88-nucleotide RNA, respectively, ending with the 3' ACCA acceptor stem sequence of tRNA. Using a 0.1 mg/ml final concentration of T7 RNA polymerase, 7–8 µg of tRNA were produced per µg of DNA template. Although Milligan and Uhlenbeck ((1989) *Meth. Enzymol.* 180:51–62) have reported that short abortive transcripts are produced when transcribing small RNAs, electrophoresis on 20% denaturing gels showed only one major RNA product remaining after gel filtration chromatography (data not shown).

Construction of pALA and pFMET

Two other novel tRNAs were generated. These tRNAs were enzymatically aminoacylated with alanine and possess an AAA anticodon to allow for recognition of a poly(U) template. The first tRNA, tRNA$_e^{ALA}$(AAA), was constructed to be analogous to the E. coli elongator tRNA$^{Ala}$. M. Sprinzl et al. (1985) *Nucl. Acids Res.* 13:r1–r104. The tRNA$_e^{Ala}$(AAA) gene (pALA or SEQ. ID. NO. 3) was constructed by copying the tRNA$^{Ala}$(GGC) gene from the E. coli genome by PCR. The anticodon was changed from GGC to AAA. The procedure used for blunting, digesting, ligating transforming and screening the pSER was then followed to form pALA.

The second, tRNA$_f^{ALA}$(AAA), is analogous to and constructed by copying the E. coli initiator tRNA$_f^{Met}$. M. Sprinzl et al. (1985) *Nucl. Acids* Res. 13:r1–r104. Although the primary structure of this tRNA was modified to facilitate in vitro transcription and aminoacylation, the features believed to be necessary for initiator function were maintained. These features include a non-Watson-Crick base pair at the end of the acceptor stem (B. L. Seong et al. (1987) *Proc. Natl. Acad. Sci. USA* 84:334–338: H. Wakao et al. (1989) *J. Biol. Chem.* 264:20363–20371), a pyrimidine-11-purine-24 base pair in the dihydrouridine stem (B. L. Seong et al (1987)), and a series of guanine and cytosine residues in the anticodon stem which form three consecutive G-C base pairs (B. L. Seong et al. (1987)).

The following modifications were made to the wild-type tRNA$_f^{Met}$ in generating the tRNA$_f^{Ala}$(AAA) gene (pFMET or SEQ. ID. NO. 4): A's were substituted for bases C and T in the anticodon of the gene forming an AAA anticodon; G's were substituted for bases 1C and 3C; T's substituted for bases 70G and 72A; and an A was inserted between bases 17C and 17aT of the gene. The procedure used for blunting, digesting, ligating transforming and screening the pSER was then followed in generating pFMET.

In Vitro Transcription

Plasmid DNA was prepared for transcription by digestion with BstNI (3) U/μg for one h at 60° C. The mixture was phenol-extracted and the DNA was ethanol-precipitated. The linearized DNA (40 μg) was added to a 2-ml transcription reaction containing 50 mM Hepes-KOH (pH 7.6), 10 mM dithiothreitol, 50 mM NaCl, 4 mM spermidine, 25 mM MgCl$_2$, 1.6 mM GTP, 4 mM GMP, ATP, CTP, UTP, 50 U RNasin, and 0.1 mg/ml T7 RNA polymerase. After incubating 2 h at 37° C., template DNA was digested with 100 U of RNase-free DNase I. Short abortive transcripts, dNTPs, and rNTPs were separated from the tRNA transcripts by gel filtration using Spectra-Gel A202 equilibrated with 10 mM Tris-HCl (pH 7.6), 1 mM EDTA, and 150 mM NaCl. The tRNA fraction was extracted once with phenol/chloroform/isoamyl alcohol (25:24:1), once with chloroform/isoamyl alcohol (24:1), then ethanol-precipitated twice.

Aminoacylation of tRNAs

Synthetic RNAs were aminoacylated using wheat germ synthetases present in the 0–70% ammonium sulfate precipitated proteins of the S150. S. Lax et al. (1986) *Meth. Enzymol.* 118:109–128. A typical mixture contained 100 mM Hepes-KOH (pH 7.8), 15 mM Mg(OAc)$_2$, 2 mM spermidine, 5 mM dithiothreitol, 5 mM ATP, 30 μM respective radioactive amino acid (100 Ci/mol), 0.8 mg/ml synthetase fraction and 0.5–1 A$_{260}$ of tRNA/ml and was incubated to 20 min at 27° C. Efficiency of aminoacylation was determined by precipitating the tRNA with trichloroacetic acid and measuring the radioactivity in the filtered precipitate by liquid scintillation counting.

Although the tRNA$^{Cys}$(AAA) was generated from the gene for *E. coli* wild type tRNA$^{Cys}$, it could not be aminoacylated by the synthetase in the *E. coli* S150 fraction. The synthetases containing 0–70% ammonium sulfate fraction of the wheat germ S150 did aminoacylate tRNA$^{Cys}$(AAA). This enzyme fraction also efficiently aminoacylated the synthetic tRNA$^{Ser}$(AAA). Based on translation reactions containing only the *E. coli* S150 fraction, the tRNA$^{Ser}$(AAA) could also be aminoacylated reasonably well by the *E. coli* synthetases (Table 1).

Yeast tRNA$^{Phe}$ was aminoacylated using an *E. coli* S150 fraction as the aminoacyl tRNA-synthetase source. B. Hardesty et al. (1971) *Meth. Enzymol.* 20:316–330. tRNA$^{Ser}$(AAA), tRNA$_e^{Ala}$(AAA) and tRNA$_f^{Ala}$(AAA) were aminoacylated using the wheat germ synthetase fraction described above. For use in the nonenzymatic initiation of translation, Phe-tRNA, Ser-tRNA, Ala-tRNA$_e^{Ala}$(AAA) and tRNA$_f^{Ala}$(AAA) were acylated on their α-amino groups by the procedure of Rappoport and Lapidot ((1974) *Meth. Enzymol.* 29:685–688).

The efficiency of aminoacylation was different for the synthetic tRNA species. The in vitro transcribed tRNA$^{Cys}$(AAA) could be aminoacylated to only about 20%, whereas over 55% of the tRNA$^{Ser}$(AAA) was aminoacylated by the wheat germ synthetases (data not shown). Unfortunately the Cys-tRNA$^{Cys}$(AAA) was unstable which prevented its isolation after aminoacylation.

The instability of the Cys-tRNA$^{Cys}$(AAA) prevented subsequent purification; however, the aminoacylation reaction could be combined with the *E. coli* translation reaction for further study. Conversely, the Ser-tRNA$^{Ser}$(AAA) was very stable throughout repeated manipulations as its was purified and labeled with coumarin.

Aminoacylation of tRNA$_e^{Ala}$(AAA) routinely reached about 60% (pmol Ala incorporated/pmol tRNA) using the wheat germ synthetases or the tRNA-depleted *E. coli* S-150 fraction as the source of amino-tRNA synthetase. Aminoacylation of tRNA$_f^{Ala}$(AAA) reached about 20% with either synthetase preparation. In no case was either tRNA observed to be aminoacylated with any amino acid other than alanine (data not shown).

TABLE 1

The poly(U)-directed synthesis of polyphenylalanine, polycysteine and polyserine.
All reactions were non-enzymatically initiated by prebinding 60 pmol AcPhe-tRNA or AcSer-tRNA (at a concentration equal to that of the ribosomes) for 5 min at 37° C.
All samples at 37° C. were incubated for 30 min at which
time they were made 0.1 M in NaOH and incubated 15 min at room temperature to hydrolyze the tRNA-amino acid bond. The proteins in the reaction mixture were then precipitated with trichloroacetic acid and filtered. The filters were dried and their radioactivity determined. Samples at 28° C. were incubated 120 min before [$^{35}$S]cysteine incorporation was measured.

| Polypeptide | Reaction Temp. (°C.) | Amino acids Incorp. (pmol) | Erythromycin | Inhibition (%) |
|---|---|---|---|---|
| Initiated with ACPhe-tRNA | | | | |
| Poly(Phe) | 37 | 1549 | — | |
| | | 1617 | + | −5 |
| Poly(Cys) | 37 | 99 | — | |
| | | 58 | + | 41 |
| | 28 | 247 | — | |
| Poly(Ser) | 37 | 499 | — | |
| | | 47 | + | 91 |
| Initiated with AcSer-tRNA | | | | |
| Poly(Phe) | 37 | 1801 | — | |
| | | 1797 | + | 0 |
| Poly(Cys) | 28 | 176 | — | |
| | | 116 | + | 34 |

TABLE 1-continued

The poly(U)-directed synthesis of polyphenylalanine, polycysteine and polyserine.
All reactions were non-enzymatically initiated by prebinding 60 pmol AcPhe-tRNA or
AcSer-tRNA (at a concentration equal to that of the ribosomes) for 5 min at 37° C.
All samples at 37° C. were incubated for 30 min at which
time they were made 0.1 M in NaOH and incubated 15 min at room temperature to
hydrolyze the tRNA-amino acid bond. The proteins in the reaction mixture were
then precipitated with trichloroacetic acid and filtered. The filters were dried
and their radioactivity determined. Samples at 28° C. were incubated 120
min before [$^{35}$S]cysteine incorporation was measured.

| Polypeptide | Reaction Temp. (°C.) | Amino acids Incorp. (pmol) | Erythromycin | Inhibition (%) |
|---|---|---|---|---|
| Poly(Ser) | 37 | 593 | − | |
| | | 67 | + | 89 |

In Vitro Translation Using Synthetic tRNAs

To examine the activity of synthetic to tRNA$^{Cys}$(AAA) and tRNA$^{Ser}$(AAA), each was used for poly-(U)-dependent polypeptide synthesis. The poly(U)-dependent incorporation of [$^{14}$C]phenylalanine into polyphenylalanine was measured as described in O. Odom et al. (1980). For nonenzymatic initiation, 0.6 μM AcPhe-tRNA or AcSer-tRNA was prebound to 0.6 μM E. coli ribosomes in the presence of poly(U) for 10 min at 37° C. W. D. Picking et al. (1990). In order to examine erythromycin sensitivity, the antibiotic was added to a final concentration of 5 μM prior to the preincubation step. [$^{14}$C]serine incorporation into polyserine was carried out exactly as polyphenylalanine synthesis was except that E. coli tRNA$^{Phe}$ was substituted with 1.17 A$_{260}$/ml synthetic tRNA$^{Ser}$(AAA). Elongation was started by the addition of an E. coli S150 fraction in a final volume of 100 μl.

The translation assay was modified to facilitate the poly(U)-dependent synthesis of polycysteine. AcPhe-tRNA or AcSer-tRNA (60 pmol) was prebound to 60 pmol ribosomes as described above. The mixture was then made to 100 μl with everything required for translation except tRNA and amino acid. To start polycysteine synthesis, the Cys-tRNA$^{Cys}$(AAA) aminoacylation reaction described above was coupled to the translation mixture by adding equal volumes of each, giving a final reaction volume of 200 μl. The reaction was then incubated at 37° C. for 30 min or at 28° for 120 min to allow for reaminoacylation of the tRNA$^{Cys}$(AAA) by the wheat germ cysteinyl-tRNA synthetase. In order to examine the conformation and environment of each nascent peptide, either CPM-Phe-tRNA and CPM-Ser-tRNA were prebound as described above. To ensure that most of the fluorophore was actually bound, the concentration of the fluorescent aminoacyl-tRNA analogues were reduced to about 10% of the ribosomes concentration. CPM labeling of the amino acid group of each of the two synthetic [$^{14}$C]alanyl-tRNAs also was performed as described previously for natural and synthetic tRNAs. The CPM-Ala-tRNA was purified by C$_1$ reversed-phase high performance liquid chromatography essentially as described for CPM-Ser-tRNA$^{Ser}$(AAA).

The results of in vitro translation using the synthetic Cys- and Ser-tRNAs and wild-type tRNA$^{Phe}$ are shown in Table 1. Cysteine incorporation was measured at both 28° and 37° C. The lower temperature allowed for greater reaminoacylation of the tRNA$^{Cys}$(AAA) by the wheat germ enzyme. All translation reactions were non-enzymatically initiated with AcPhe-tRNA or AcSER-tRNA which was prebound at a 1:1 molar ratio with the ribosomes in the presence of poly(U). Six types of reaction mixtures with ribosomes bearing nascent polypeptides were generated, three each with N-AcPhe and N-AcSer at the amino-terminus, respectively. The sensitivity of the synthesis of each polypeptide to inhibition by 5 μM erythromycin was also tested. In parallel, [$^{14}$C]AcPhe-tRNA was used to initiate each of the polypeptides in the presence of unlabeled amino acid in order to estimate the number of ribosomes which are fully active in synthesizing each type of nascent peptide (data not shown).

Over 1500 pmol of phenylalanine were incorporated into polyphenylalanine in the presence or absence of the erythromycin (Table 1). It was determined that 30% (18 pmol) of the ribosomes in the reaction mixtures were active in polyphenylalanine synthesis. Using this value, it was calculated that the nascent polyphenylalanine peptides were about 80 amino acids in length. Since synthetic tRNA$^{Ser}$(AAA) could be aminoacylated by the crude E. coli S150 fraction, polyserine synthesis was carried out in the same manner as polyphenylalanine synthesis. In this case, however, only about 500 pmol of serine were incorporated into polyserine. This synthesis was inhibited by about 90% by erythromycin (Table 1). Only about 10% of the ribosomes were active in the polyserine synthesis, however, which also gives an average peptide length of about 80 amino acids (data not shown).

At 37° C., 99 pmol of cysteine were incorporated into polycysteine in 30 min which was inhibited 41% by erythromycin (Table 1). It was estimated that 15% (10 pmol) of the ribosomes were active in the polycysteine synthesis which corresponds to an average peptide length of about 10 amino acids. It should be noted that this synthesis was carried out with a coupled wheat germ aminoacylation: E. coli translation system. Only very limited reaminoacylation of the tRNA by the wheat germ synthetase can occur at 37° C. To adjust for this, polycysteine synthesis was also initiated at 28° C. and carried out at this temperature for 120 min (Table 1). In this case, 247 pmol of cysteine were incorporated. As at 37° C., 10 pmol of ribosomes were active in polycysteine synthesis, which gives an average peptide length of about 25 amino acids in this case.

A greater amount of polyphenylalanine synthesis (longer average peptide length; higher proportion of ribosomes with nascent peptides) in the poly(U)-directed translation system may reflect the atypical properties of phenylalanine peptides. Short phenylalanine peptides appear to precipitate more readily with trichloroacetic acid than short peptides of serine or cysteine. This may contribute to relatively larger total amount of phenylalanine incorporation, and is likely to be a major factor responsible for the relatively lower percentage of ribosomes which appear to be active in polyserine or polycysteine synthesis. Another factor that may contribute to the relatively large value for total phenylalanine incorporation is the extended time over which nearly linear rate of peptide synthesis is sustained when polyphenylalanine is being formed. The decrease in the rate of peptide synthesis that is observed with most peptides other than polyphenylalanine may reflect product inhibition. Spirin et al. ((1988) Science 242:1162–1164) have observed almost linear rates of synthesis for many hours if the peptide product is removed from the reaction mixture as it is formed. Nascent polyphenylalanine peptides are so insoluble that they may be effectively removed from solution in the reaction, thus leading to a situation equivalent to that produced in the continuous flow translation system.

The results presented in Table 1 also demonstrate that poly(U)-directed synthesis of polycysteine and polyserine from the synthetic tRNAs are sensitive to inhibition by erythromycin. In contrast, polyphenylalanine synthesis is not inhibited by the antibiotic under the same conditions. This is consistent with previous observation ((G. Chinali et al. (1988) Biochim. Biophy. Acta 949:71–78; T. Otaka et al. (1975) Proc. Natl. Acad. Sci. USA 72:2649–2652; D. Vasquez (1979) Molecular Biology Biochemistry and Biophysics Springer-Verlag, Berlin, vol. 30, p. 312) and supports the hypothesis that this difference in sensitivity to erythromycin is a result of the properties of the nascent peptide itself.

Poly(U)-dependent polypeptide synthesis was attempted using Ala-tRNA$_e^{Ala}$(AAA) and Ala-tRNA$_f^{Ala}$(AAA). Polypeptide synthesis was facilitated by prebinding N-acetyl derivatives of Phe-tRNA, Ala-tRNA$_e^{Ala}$(AAA) and Ala-tRNA$_f^{Ala}$(AAA). N-acetylation of the aminoacyl-tRNAs was carried out with the N-hydroxysuccinimide ester of acetic acid according to the method of Rappoport and Lapidot (1974). Nonenzymatic tRNA binding to ribosomes was performed in 50 mM Tris-HCl (pH 7.5), 100 mM NH$_4$Cl, 15 mM Mg(OAc)$_2$, 5 mM 2-mercaptoethanol, 0.2 mg/ml poly(U), 0.5 µM ribosomes and 0.5 µM acylated tRNA. Polyalanine synthesis was initiated as described previously for polyphenylalanine (W. D. Picking et al. (1991) J. Biol. Chem. 266:1534–1542) and polyserine as described above except that [$^{14}$C]alanine and either tRNA$_e^{Ala}$(AAA) or tRNA$_f^{Ala}$(AAA) were used as the amino acid and tRNA sources. tRNA$_e^{Ala}$(AAA) was used at a final concentration of 1 A$_{260}$ units/ml while tRNA$_f^{Ala}$(AAA) was used at a concentration of about 3 A$_{260}$ units/ml to reach nearly similar amounts of aminoacylated tRNA in all polyalanine assays. The incorporation of [$^{14}$C]alanine into polyalanine was determined as described previously in W. D. Picking et al. (1991).

Figure 2:
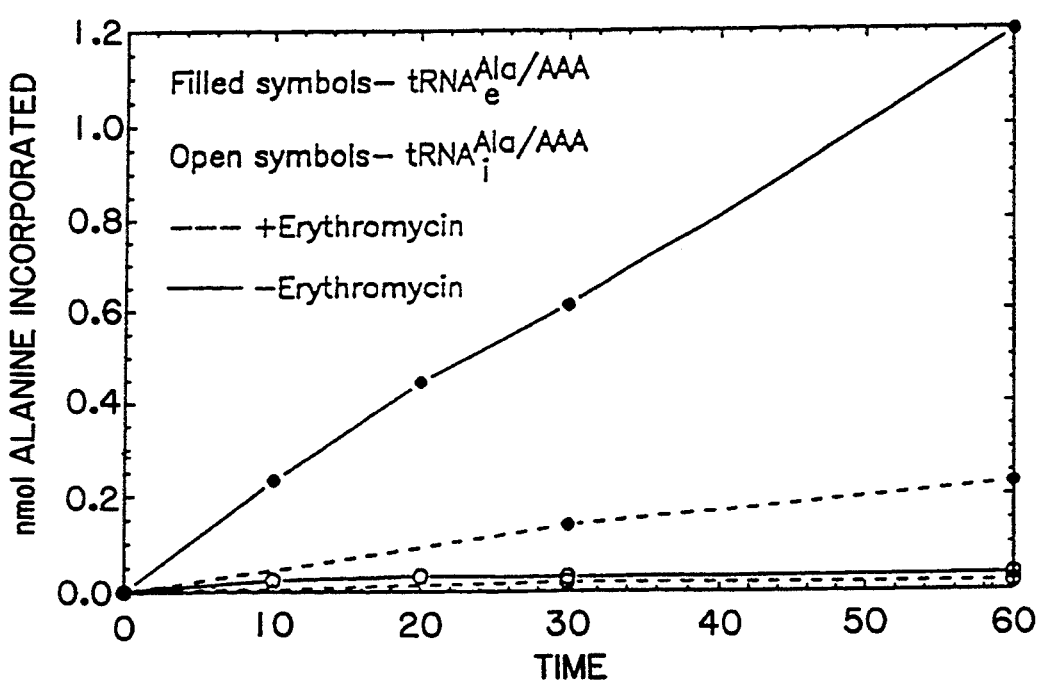
FIG. 2 is the anisotropy of fluorescence from probes at the amino terminus of nascent peptides during poly-(U)-directed elongation. Polypeptide synthesis was initiated with either CPM-Phe-tRNA (A) or CPM-Ser-tRNA (B) and the anisotropy monitored over time. In A and B, polyphenylalanine synthesis is shown with open triangles and dotted lines ( . . . ), polycysteine synthesis is shown with open circles and dashed lines ( - - - ) and polyserine synthesis as shown by closed circles and solid lines (—). Anisotropy is measured over a 60 min period at 20° C. with fluorescence excitation at a wave length of 385 nm and emission at a wave length of 475 nm.

Only tRNA$_e^{Ala}$(AAA) supported poly(U)-dependent polyalanine synthesis (FIG. 2). Synthetic elongator tRNA-dependent polyalanine synthesis was linear for more than 60 min at 37° C. (FIG. 2) and for longer than 2 h at 20° C. (data not shown). Conversely, when tRNA$_f^{Ala}$(AAA) was used, polyalanine synthesis was only slightly above background levels (FIG. 2). An interesting feature of polyalanine synthesis in this system is that it is sensitive to inhibition by erythromycin (FIG. 2). This is in contrast to polyphenylalanine synthesis which is resistant to erythromycin (W. D. Picking et al. (1991)).

Tests were then undertaken to determine if AcAla-tRNA$_f^{Ala}$(AAA) or AcAla-tRNA$_e^{Ala}$(AAA) could be nonenzymatically prebound to ribosomes to facilitate polyalanine synthesis. Incorporation of alanine into polyalanine from Ala-tRNA$_e^{Ala}$(AAA) was similar whether AcAla-tRNA$_e^{Ala}$(AAA), AcAla-tRNA$_f^{Ala}$(AAA) or AcPhe-tRNA was prebound to poly(U)-programmed 70S ribosomes (Table 2). The number of nascent polyalanine chains synthesized was determined by measuring the incorporation of radiolabeled amino acid from prebound Ac-[$^{14}$C]aminoacyl-tRNA followed by polyalanine synthesis in the presence of unlabeled alanine. It was possible to estimate the length of the nascent polyalanine chains from parallel determinations of radioactive alanine incorporation and knowing the number of nascent chains synthesized. The length of the nascent peptides produced was similar regardless of the initiating tRNA (Table 2). The important feature of these data is that while tRNA$_f^{Ala}$(AAA) is not functional for peptide elongation, it is able to bind at the ribosomal P site to allow nonenzymatically-initiated peptide synthesis. It should be noted, also, that polyalanine synthesis was inhibited by erythromycin regardless of the initiating acyl-tRNA (even AcPhe-tRNA; data not shown).

TABLE 2

Polyalanine Synthesis after Prebinding Three Different N-blocked Aminoacyl-tRNAs

| Initiating Nascent tRNA | pmol Ala incorporated | Nascent chains initiated pmol | chain length |
|---|---|---|---|
| AcPhe-tRNA | 676 | 18 | 38 |
| AcAla-tRNA-$_e^{Ala/AAA}$ | 626 | 13 | 52 |
| AcAla-tRNA$_f^{Ala/AAA}$ | 614 | 14 | 44 |

Ac[$^{14}$C]aminoacyl-tRNA was used in the presence of nonradiative alanine to determine the number of nascent chains initiated. [$^{14}$C] Alanine was used to measure pmol Ala incorporated into polyalanine. The average length of nascent polyalanine is given by pmol Ala/pmol nascent chains as described in Methods.

The fluorescence properties of a CPM residue on the α-amino group of these two aminoacylated alanine tRNAs reflect the local environment around the fluorophore when the tRNAs are either free in solution or bound to ribosomes. CPM-Ala-tRNA$_e^{Ala}$(AAA) binds to 70S ribosomes with many of the same properties we have previously reported by W. D. Picking et al. (1991) for CPM-Phe-tRNA and synthetic CPM-Ser-tRNA$^{Ser}$(AAA) discussed above. For CPM-Ala-tRNA$_f^{Ala}$(AAA), however, the fluorescence anisotropy data indicate that the fluorphore is held more rigidly than that of its elongator counterpart when each is free in solution. Conversely, the fluorophore on the initiator tRNA analogue appears to be able to move more freely than the same probe on the elongator tRNA once it is bound to 70S ribosomes. In addition, although each fluorescent tRNA binds to the ribosomal "P site", each responds differently to the subsequent binding of erythromycin. Considered together these results suggest that the CPM probe and presumably the alanine to which it is linked are not in identical positions when the two tRNAs are in the "P site" as judged by function. This difference in binding relative to the binding site of erythromycin does not prevent the antibiotic from inhibiting polyalanine synthesis whether this synthesis is started by prebinding N-blocked elongator Ala-tRNA, initiator Ala-tRNA or Phe-tRNA.

These functional differences may reflect differences in the structure of initiator and elongator tRNAs. There are many regions which are strongly conserved among prokaryotic initiator tRNAs that contrast them to elongator tRNAs. B. L. Seong et al. (1987); H. Wakao et al. (1989); and C. O. Gualerzi et al., (1990) *Biochem.* 29:5881-5889. These features include the absence of a Watson-Crick base pair between residues 1 and 72, the presence of a purine 11-pyrimidine 24 base pair in the dihydrouridine stem (D-stem), and three consecutive G·C base pairs in the anticodon stem. B. L. Seong et al. (1987). The latter feature may be involved in discriminating initiator tRNAs from elongator tRNAs and is a requirement for P-site specific binding to ribosomes. B. L. Seong et al. (1987). Site-specific mutations in this portion of the anticodon stem has been shown to lead to a progressive loss of initiator function for tRNA$_f^{Met}$. The appearance of three consecutive G·C base pairs has also been suggested to give the anticodon of initiator tRNAs special structural and electromagnetic properties. K. A. Sharp et al. (1990) *Biochem.* 29:340-346.

Fluorescence Measurements of the Extension of Novel Nascent Polypeptides

First, CPM-Phe-tRNA or CPM-Ser-tRNA were used to initiate poly(U)-dependent synthesis of polyphenylalanine, polycysteine, and polyserine. CPM labeling of the α-group of yeast Phe-tRNA is described in O. Odom et al. (1990). Ser-tRNA$^{Ser}$(AAA) was similarly labeled at the α-group of the seryl moiety. The fluorescent tRNA analogues were purified by reversed-phase HPLC on a $C_1$ column in a manner similar to that described for CPM-Phe-tRNA.

Steady-state fluorescence measurements were carried out on a Model 8000 photon-counting spectrofluormeter from SLM-Aminco Instruments, Inc. (Urbana, Ill.) as previously described in W. Rychlik et al. ((1983) *Biochemistry* 22:85-93). Spectral data were accumulated at 1-nm intervals with a scanning rate of 0.5 sec per wave length increment. All measurements were automatically corrected for the wavelength dependence of the photomultiplier sensitivity. Fluorescence measurements were made at an absorbance of less than 0.1 at the excitation wavelength in a volume of 0.5 ml and at a temperature of 20° C. to intentionally slow the rate of elongation. Steady-state fluorescence anisotropy measurements were made as described in O. Odom ((1984) *Biochemistry* 23:5069-5076).

The anisotropy of fluorescence from the CPM probe on these amino acids was followed as the nascent peptides were formed. Binding of CPM-Phe-tRNA into peptidyl transferase center of ribosomes results in an increase in the fluorescence anisotropy from 0.18 to about 0.36. This high fluorescence anisotropy reflects the rigidity with which the amino acid of CPM-Phe-tRNA is held in the peptidyl transferase center. W. D. Picking et al. (1990). Synthesis of the first few peptide bonds of the polyphenylalanine resulted in a drop in the anisotropy which then increased as the nascent peptide was extended. In contrast, poly(A)-dependent polylysine synthesis resulted in a rapid drop in the anisotropy as the amino-terminal probe was extended from the peptidyl transferase center without any subsequent increase in anisotropy.

Figure 3A:
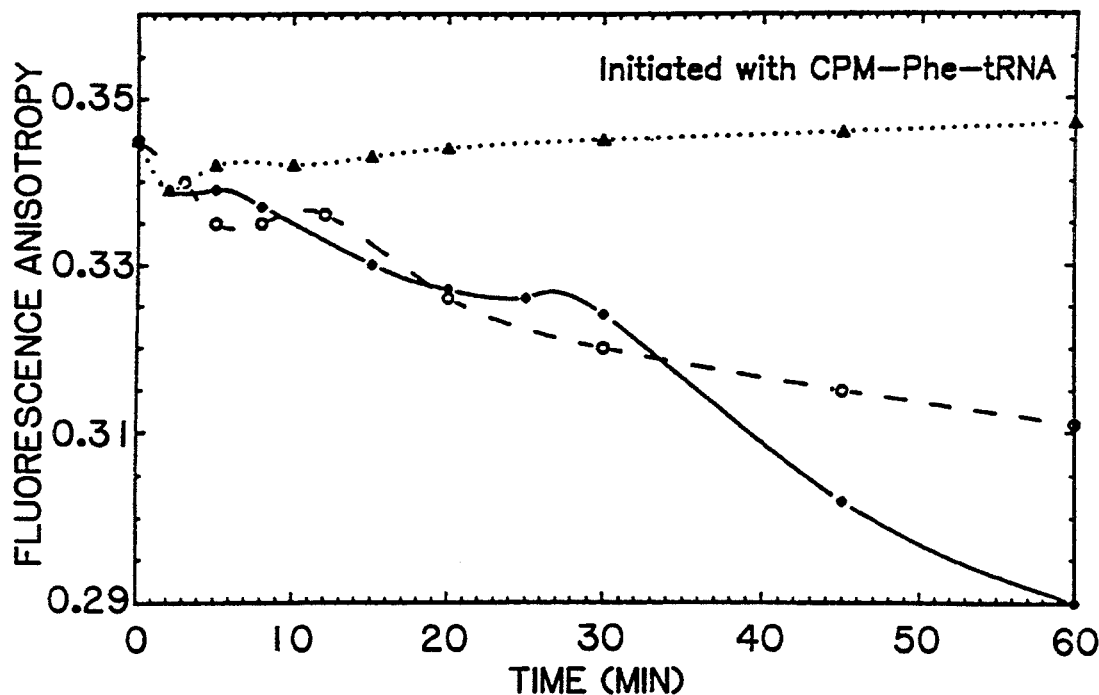
FIGS. 3A and 3B are the poly(U)-directed synthesis of polyalanine with tRNA$_e^{Ala}$(AAA).

Upon initiation of polycysteine or polyserine synthesis with CPM-Phe-tRNA, anisotropy drastically dropped in a manner somewhat similar to that seen previously with polylysine (FIG. 3A). Unlike polylysine synthesis, however, the anisotropy of these nascent peptides consistently leveled off for brief periods before once again dropping (FIG. 3A). These results could be expected if the amino termini of both nascent peptides were exiting the ribosomes within a length of a few amino acids from the peptidyl tRNA center. Nascent serine peptides are longer than those of cysteine (Table 1) which may account for the lower final anisotropy of the former. Based on this and previous results, it can be suggested that polycysteine and polyserine nascent polypeptides are extended directly into the surrounding solution much like poly(A)-directed nascent polylysine.

Figure 3B:
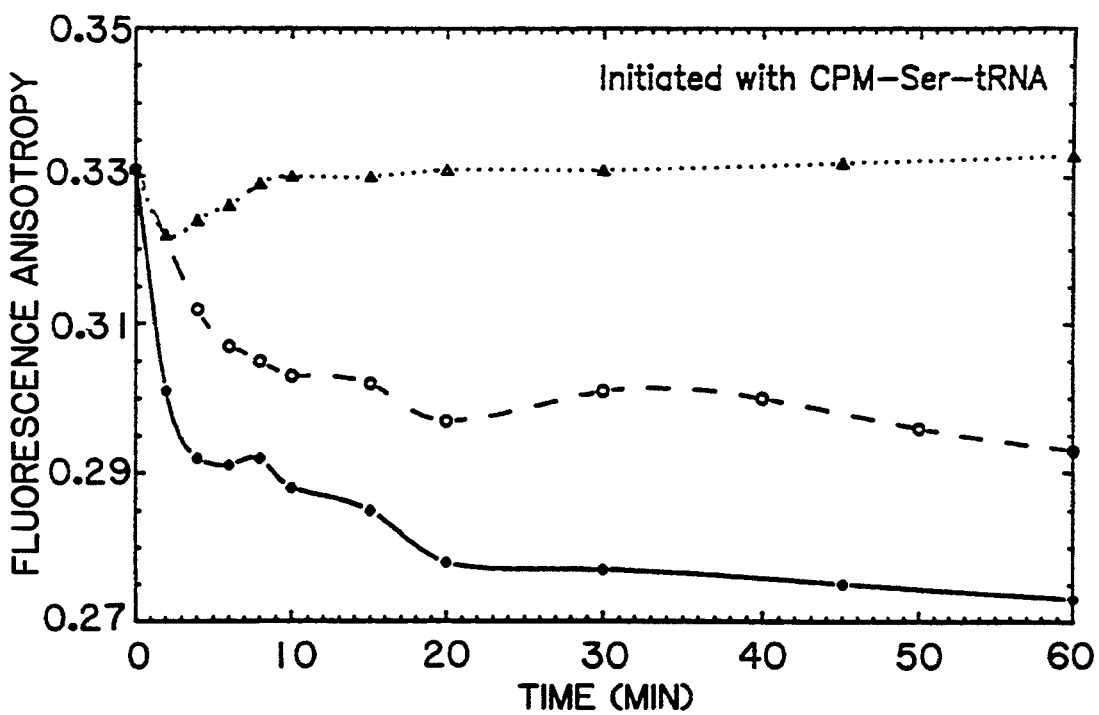

In order to provide further evidence that the results described above were not a result of the CPM-Phe-tRNA used to initiate translation, each nascent polypeptides species, including polyphenylalanine, was initiated with CPM-Ser-tRNA. The changes in fluorescence that occurred as the peptides were elongated were monitored as described above. As seen previously, anisotropy decreased as the first peptide bonds of the polyphenylalanine were formed and then increased as the peptide was extended (FIG. 3B; W. D. Picking et al. (1990)). The anisotropy of the CPM-Ser probe also decreased significantly as the first peptide bonds of the polycysteine and polyserine peptides were formed. However, in contrast to the results for polyphenylalanine, it did not increase as the polypeptides were extended. Interestingly, the decline in anisotropy stopped for a brief period after a few amino acids (estimated 3 or 4) had been added to the amino terminal CPM-Ser (FIG. 3B). The results are similar to those obtained when peptides were initiated with CPM-Phe. The basis for this result is unclear. It may reflect the confirmation of the short nascent peptide or a special structural feature of the ribosomes that the probe encounters as the peptide is initially extended.

For estimation of the average length of nascent polyalanine chains (given in Table 2) it was necessary to experimentally determine the number of active ribosomes in the poly(U)-dependent polypeptide assay described above. To do this, 55 pmol of Ac[$^{14}$C]Phe-tRNA (100 Ci/mol), Ac[$^{14}$C]Ala-tRNA$_e^{Ala}$(AAA) or Ac[$^{14}$C]Ala-tRNA$_f^{Ala}$(AAA) (50 Ci/mol) was prebound to poly(U)-programmed ribosomes (50 pmol) by incubation at 37° C. for 15 min prior to the addition of the other components required for protein synthesis. After prebinding the Ac[$^{14}$C]aminoacyl-tRNA, polypeptide synthesis was carried out as described above, except that nonradioactive alanine was used so that the only radioactivity incorporated into trichloroacetic acid precipitable material was from prebound N-blocked amino acids. This provides a measure of those ribosomes on which the amino acid from prebound [$^{14}$C]-labeled Ac-aa-tRNA was subsequently incorporated into nascent polyalanine. When the total pmol of alanine incorporated into polyalanine (described above) is measured, the value can be divided by the number of active ribosomes (as determined by measuring the number of nascent chains synthesized) to give an estimate of the average nascent polyalanine chain length.

TABLE 3

Fluorescence Properties of CPM-Ala-tRNA$_e^{Ala/AAA}$ and CPM-Ala-tRna$_f^{Ala/AAA}$

| tRNA species | position | anisotropy | quantum yield | Em$_{max}$(nm) |
|---|---|---|---|---|
| CPM-Ala-tRNA$_e^{Ala/AAA}$ | free | 0.185 | 0.393 | 479 |
| | bound (P site) | 0.346 | 0.503 | 473 |
| | bound (A site)[1] | 0.312 | 0.472 | 475 |
| CPM-Ala-tRNA$_f^{Ala/AAA}$ | free | 0.205 | 0.449 | 478 |
| | bound (P site) | 0.310 | 0.516 | 475 |

TABLE 3-continued

Fluorescence Properties of CPM-Ala-tRNA$_e^{Ala/AAA}$ and CPM-Ala-tRna$_f^{Ala/AAA}$

| tRNA species | position | anisotropy | quantum yield | Em$_{max}$(nm) |
|---|---|---|---|---|
| | bound (A site)[1] | 0.208 | 0.466 | 478 |

[1]Deacylated tRNA$^{Phe}$ was prebound to poly(U)-programmed ribosomes in a 1.1:1 ratio prior to the binding of the fluorescent tRNA species.

Again a model 8000 proton-counting spectrofluorometer from SLM-Aminco Instruments, Inc. (Urbana, Ill.) was used for steady-state fluorescence measurements as described above. Fluorescent tRNAs were bound to ribosomes as described above except that the concentration of these tRNAs was reduced to about 10% of the ribosome concentration to ensure maximum tRNA binding. Spectra were measured at 1-nm emission intervals at a scanning rate of 0.5 sec per wavelength increment with an excitation wavelength of 385 nm. Anisotropy and relative intensity measurements were carried out at an emission wavelength of 475 nm. Measurements were automatically corrected for the wavelength dependence of photomultiplier sensitivity. Fluorescence measurements were carried out at 20° C. in a volume of 0.6 ml. All measurements were made with a simple absorbance of less than 0.1 at the excitation wavelength and fluorescence anisotropy measurements were made as previously described in W. L. Picking et al. (1991). The quantum yields of CPM-Ala-tRNA$_e^{Ala}$(AAA) and CPM-Ala-tRNA$_f^{Ala}$(AAA) were determined by comparison with quinine sulfate in 0.05M H$_2$SO$_4$ which has a quantum yield of 0.508 at 25° C. (R. A Velapold et al. (1980) "A Fluorescence Standard Reference Manual: Quine Sulfate Dihydrate," National Bureau of Standards Special Publication 260–64, U.S. Government Printing Office, Washington, D.C.).

Interestingly, the fluorescence anisotropy and quantum yield differed for the two tRNAs under the conditions examined. The anisotropy of free CPM-Ala-tRNA$_e^{Ala}$(AAA) (0.185) was similar to that seen previously for the natural elongator tRNA CPM-Phe-tRNA$^{Phe}$ (0.181) as well as the synthetic elongator tRNA CPM-Ser-tRNA$^{Ser}$(AAA) (0.175). Upon binding to 70S ribosomes the anisotropy and quantum yield of the CPM-Ala-tRNA$_e^{Ala}$(AAA) increased in the same way as previously studied tRNAs (W. D. Picking et al. (1991); Table 3). Conversely, CPM-Ala-tRNA$_f^{Ala}$(AAA) had a higher anisotropy when free in solution (0.205) and a lower anisotropy when bound at the ribosomal P site (0.310) in comparison to free (0.185) and P site-bound (0.346) CPM-Ala-tRNA$_e^{Ala}$(AAA) (Table 3). That P site binding of each tRNA had occurred was confirmed by the addition of puromycin. This resulted in a large decrease in the anisotropy of bound CPM-Ala-tRNA$_e^{Ala}$(AAA) (to 0.175) and CPM-Ala-tRNA$_f^{Ala}$(AAA) (to 0.183) as each CPM-Ala-puromycin product was formed and subsequently released from the ribosome (data not shown).

When deacylated tRNA$^{Phe}$ was prebound to the 70S ribosomes to promote A site binding of CPM-Ala-tRNA$_f^{Ala}$(AAA), no change in the quantum yield, anisotropy or emission spectrum was observed indicating that no binding had occurred (Table 3). This was confirmed by experiments demonstrating that, after prebinding of deacylated tRNA$^{Phe}$, the CPM-Ala-tRNA$_f^{Ala}$(AAA) did not remain with the ribosome fraction when the reaction components were separated by gel filtration on Sephacryl S-300 (data not shown). Conversely, CPM-Ala-tRNA$_e^{Ala}$(AAA) appeared to bind at the ribosomal A site as judged by increased anisotropy (0.312) and quantum yield (0.472) (Table 3). Typically less than 10% of this A site-bound CPM-Ala-tRNA$_e^{Ala}$(AAA) was reactive with puromycin (data not shown).

The data suggest that the synthetic initiator tRNA has retained the binding properties of natural tRNA$_f^{Met}$. These properties are paralleled by fluorescence characteristics that differ from those of the elongator Ala-tRNA.

CPM-Ala-tRNA$_e^{Ala}$(AAA) and CPM-Ala-tRNA$_f^{Ala}$(AAA) (25 pmol) also were used to examine the effect of IF-2 on tRNA binding to 30S and 70S ribosomes. Fluorescence anisotropy and quantum yield were measured in the presence and absence of purified IF-2 (105 pmol) after the sequential addition of 30S subunits (195 pmol) and 50S subunits (195 pmol). Measurements were taken in 50 mM Tris-HCl (pH 7.5), 6 mM Mg(OAc)$_2$, 50 mM NH$_4$Cl, 1 mM GTP, 5 mM dithioerythritol and 0.2 mg/ml poly(U) in a final volume of 600 μl. When these measurements were finished, the Mg$^{2+}$ concentration was raised to 15 mM to nonenzymatically facilitate tRNA binding and the anisotropy and quantum yield were measured again.

The results appear to indicate that neither methionine nor the AUG codon are uniquely required for peptide initiation with IF-2. Indeed, initiator tRNAs mutated to recognize UUC and GUC codons and aminoacylated with phenylalanine and valine, respectively, have been shown to intiate enzymatically active β-galactosidase in vivo when the mRNA contains the appropriate codon at the initiator codon position. R. Chattapadhyay et al. (1990) Biochem. 29:4263–4268. In a similar study, initiation of active chloramphenicol acetyltransferase can occur from an amber (UAG) codon, probably with glutamine, when an initiator tRNA altered to recognize the initiation amber codon is present. U. Varshney et al. (1990) Proc. Natl. Acad. Sci. 87:1586–1590.

TABLE 4

IF-2 Mediates the Binding of CPM-Ala-tRNA$_f^{Ala/AAA}$ to Ribosomes

| tRNA | addition | anisotropy | quantum yield |
|---|---|---|---|
| CPM-Ala-tRNA$_f^{Ala/AAA}$ | none | 0.206 | 0.449 |
| | +30S | 0.204 | 0.450 |
| | +50S | 0.238 | 0.453 |
| | +9 mM Mg$^{2+}$ | 0.308 | 0.503 |
| | +IF-2 & 30S | 0.232 | 0.440 |
| | +50S | 0.300 | 0.516 |
| | +9 mM Mg$^{2+}$ | 0.306 | 0.512 |
| CPM-Ala-tRNA$_e$Ala/AAA | none | 0.182 | 0.393 |
| | +30S | 0.187 | 0.389 |
| | +50S | 0.200 | 0.393 |
| | +9 mM Mg$^{2+}$ | 0.340 | 0.483 |
| | +IF-2 & 30S | 0.188 | 0.393 |
| | +50S | 0.197 | 0.397 |
| | +9 mM Mg$^{2+}$ | 0.343 | 0.488 |

IF-2 and/or 30S ribosomal subunits were incubated with the fluorescent tRNA for 15 min at 37° C. with 6 mM mg$^{2+}$ present before measuring fluorescence. After each subsequent addition, the reaction mixture was incubated 10 min at 37° C. and the 15 min at 20° C. (in the cuvette used for fluorescence measurements) prior to reading the fluorescence. All reactions were carried out in a final volume of 600 μl as described in Methods. Following the addition of ribosomes, the Mg$^{2+}$ concentration was increased 9 mM (to give a final concentration of 15 mM) to allow for the nonenzymatic binding of the fluorescent tRNAs. The anisotropy and quantum yield were then measuredj again for comparative purposes.

The ability of tRNA$_f^{Ala}$(AAA) to function in enzymatic peptide initiation was tested using purified E.coli initiation factor 2 (IF-2) to bind the tRNA to 30S and 70S ribosomes (in 6 mM Mg$^{2+}$). IF-2 facilitated binding of CPM-Ala-tRNA$_f^{Ala}$(AAA) to 30S subunits as judged by increased anisotropy and quantum yield (Table 4). When 50S subunits were then added to the reaction mixture, over 80% of the CPM-Ala-tRNA$_f^{Ala}$(AAA) was bound to the 70S ribosomes in 6 mM Mg$^{2+}$ as indicated by an increased fluorescence anisotropy (Table 4). Only a slight further increase in binding was observed when the Mg$^{2+}$ concentration was increased to 15 mM in the reaction mixture to mediate the nonenzymatic binding of the tRNA as discussed above (Table 4). With poly(U), at 6 mM Mg$^{2+}$, CPM-Ala-tRNA$_f^{Ala}$(AAA) did not bind to 30S ribosomal subunits in the absence of IF-2 and only poorly to 70S ribosomes (Table 4). Only after increasing the Mg$^{2+}$ to 15 mM did the initiator tRNA bind to poly(U)-programmed ribosomes in the absence of IF-2 (Table 4). These data indicate that IF-2 specifically mediates the binding of CPM-Ala-tRNA$_f^{Ala}$(AAA) to 30S ribosomal subunits or to 70S ribosomes in 6 mM Mg$^{2+}$.

CPM-Ala-tRNA$_e^{Ala}$(AAA), in contrast, did not bind to 30S or 70S ribosomes in 6 mM Mg$^{2+}$ in the presence or absence of IF-2 (Table 4); however, in each case it bound rapidly upon increasing the Mg$^{2+}$ concentration to 15 mM. At the high Mg$^{2+}$ concentration, the fluorescence anisotropy and quantum yield of CPM-Ala-tRNA$_e^{Ala}$(AAA) increased to the values previously observed for ribosome binding (see Table 3).

Figure 4A:
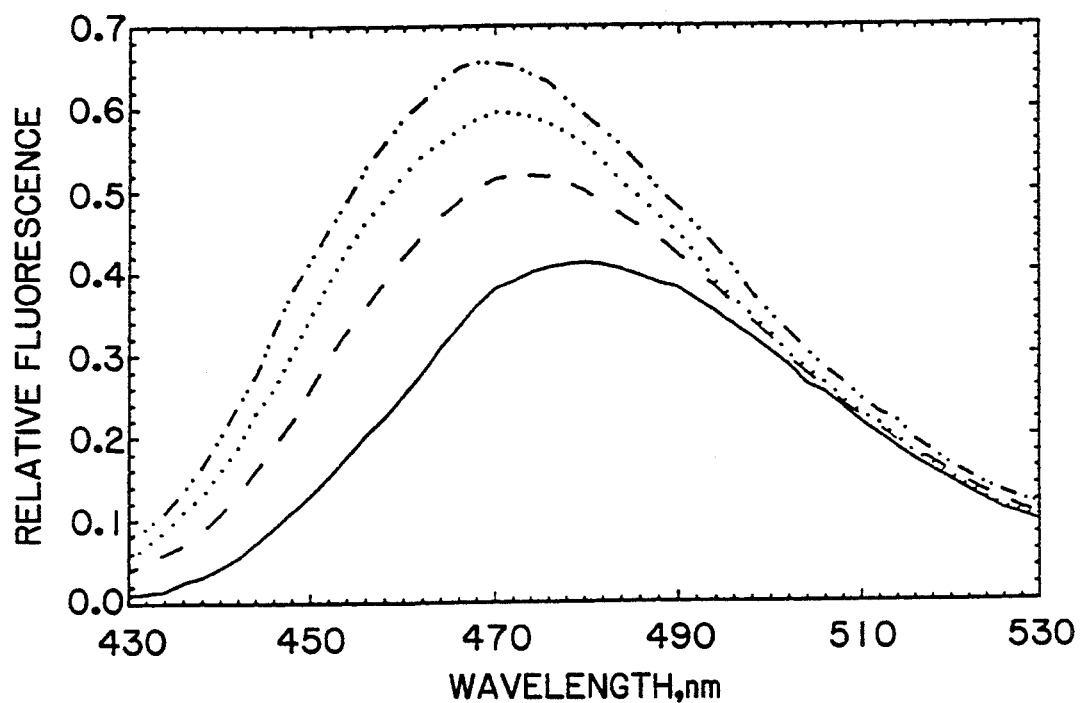
FIGS. 4A&B are the emission spectra of free and ribosome-bound elongator and initiator CPM-Ala-tRNA$^{Ala}$(AAA).

Fluorescence from the coumarin moiety of CPM is very sensitive to hydrophobicity, charge and other factors in the immediate vicinity of the probe. As with CPM-Ser-tRNA discussed above, this environmental sensitivity was used to compare the two CPM-Ala-tRNAs under different conditions. The fluorescence emission spectra of CPM-Ala-tRNA$_e^{Ala}$(AAA) and CPM-Ala-tRNA$_f^{Ala}$(AAA) were measured when the tRNAs were free in solution, bound to poly(U)-programmed ribosomes, bound to ribosomes simultaneously with erythromycin and bound to ribosomes simultaneously with sparsomycin and puromycin (FIG. 4A and B). Sparsomycin has been shown in this laboratory to bind to 70S ribosomes and inhibit puromycin reactivity with P site-bound N-acyl-Phe-tRNA without preventing the binding of puromycin (Odom and Hardesty, manuscript in preparation).

The intensity of the emission spectrum of CPM-Ala-tRNA$_e^{Ala}$(AAA) is increased and accompanied by a considerable blue shift (6 nm) upon binding to ribosomes (FIG. 4A, dashed line versus solid line). The emission of CPM-Ala-tRNA$_f^{Ala}$(AAA) undergoes a similar although somewhat smaller increase in fluorescence intensity upon binding to ribosomes (FIG. 4B, dashed line) accompanied by a slightly smaller blue shift (3 nm).

Figure 4B:
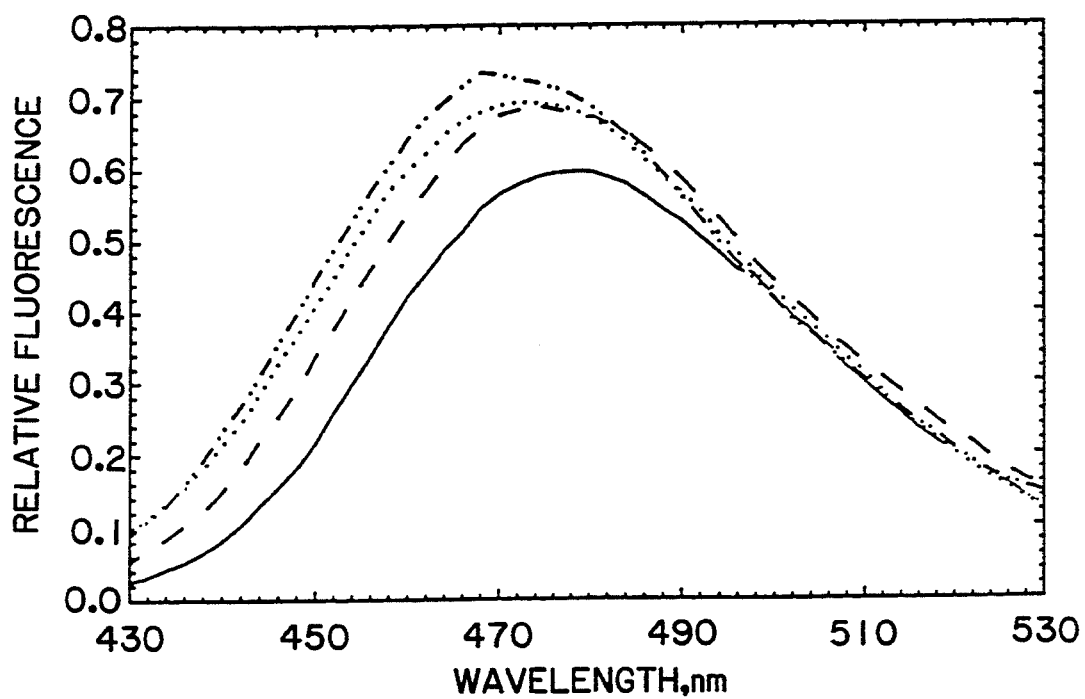
FIG. 4B in another experiment the emission spectrum of each tRNA was measured after ribosome binding. Sparsomycin was subsequently added (final concentration=5 μM). The emission spectrum was taken. Then puromycin was added to give a concentration of 0.5 mM. The emission spectrum was again measured (- - ). After measuring the emission spectrum in the presence of puromycin, the fluorescence anisotropy of each sample was measured to assure that no drop in anisotropy had occurred which would indicate puromycin reactivity.

When erythromycin was bound to ribosomes already containing CPM-Ala-tRNA$_e^{Ala}$(AAA), a 15% increase in the relative fluorescence intensity was observed accompanied by a further 3 nm blue shift in the emission maximum (FIG. 4A, dotted line). Interestingly, erythromycin resulted in only a 3% increase in the relative intensity of bound CPM-Ala-tRNA$_f^{Ala}$(AAA) accompanied by a 2 nm blue shift in the emission spectrum (FIG. 4B, dotted line). These observations suggest that the CPM-Ala moiety on the initiator tRNA is in a somewhat different position on the ribosome relative to the erythromycin binding site. To explore this possibility, the fluorescence of each tRNA (after binding to poly(U)-programmed ribosomes) was examined following the sequential addition of sparsomycin and puromycin. Sparsomycin alone had little effect on the emission spectrum of either of the fluorescent tRNAs (data not shown). However, the antibiotic is a inhibitor of the puromycin reaction with acyl-tRNA bound in the ribosomal P site. This made it possible to examine the effect of puromycin binding on the fluorescence of each tRNA (FIG. 4A and B). Puromycin binding resulted in a 26% increase in the fluorescence intensity of bound CPM-Ala-tRNA$_e^{Ala}$(AAA) accompanied by a 4 nm blue shift in the emission maximum (FIG. 4A, dash-/dot/dot line). No change in anisotropy was observed. This result confirms the inhibition of puromycin reactivity in the presence of sparsomycin. Conversely, puromycin binding resulted in only a 6% increase in the fluorescence of bound CPM-Ala-tRNA$_f^{Ala}$(AAA), also accompanied by a 4 nm blue shift (FIG. 4B, dash/dot/dot line).

The results with erythromycin and sparsomycin/puromycin support the conclusion that the CPM-Ala portion of the initiator tRNA is held in a different position on the ribosome than is the same portion of the elongator tRNA. An interesting feature of these results is that polyalanine synthesis initiated with either AcAla-tRNA is inhibited by erythromycin and each N-acyl-tRNA is puromycin-reactive (in the absence of sparsomycin) when bound in the ribosomal P site. This suggests the CPM-Ala portion of the initiator tRNA is held differently with respect to the binding sites of erythromycin and puromycin than is the same portion of the elongator tRNA without any obvious effect on the function of either antibiotic. The implications of this difference in CPM-Ala position is not clear but most likely reflects differences in the tRNA conformation rather than function in peptidyl transfer.

In summary, synthetic tRNA$^{Cys}$(AAA), although somewhat poorly aminoacylated, was efficiently used for poly(U)-directed polycysteine synthesis. The synthetic tRNA$^{Ser}$(AAA) was a much better substrate for aminoacylation and was also used efficiently in the poly(U)-directed translation system. An interesting feature of the poly(U)directed synthesis of polycysteine and polyserine was that each was sensitive to inhibition by prebound erythromycin whether non-enzymatically initiated with AcSer-tRNA or AcPHe-tRNA. This is in direct contrast to polyphenyalanine synthesis which is not affected by erythromycin whether initiated with AcPhe-tRNA or AcSer-tRNA. These data suggest that erythromycin sensitivity is a function of nascent peptide and not mRNA or tRNA.

To extend these data, the fluorescence properties of a CPM probe attached to an amino-terminal phenylalanine or serine was monitored as polyphenylalanine, polycysteine, or polyserine was formed. Whether initiated with CPM-phenylalanine or CPM-serine, polyphenylalanine behaved consistently and appeared to build up as an insoluble mass adjacent to the peptidyl transferase center. On the other hand, nascent peptides that were extended with cysteine or serine appeared to exit directly from the peptidyl transferase center into the surrounding solution whether they were initiated with AcSer-tRNA or AcPhe-tRNA. This result is similar to that seen with polylysine.

Comparing the two synthetic alanine tRNAs, the elongator tRNA (tRNA$_e^{Ala}$(AAA) and initiator tRNA (tRNA$_f^{Ala}$(AAA) behaved differently during peptide synthesis on ribosomes as judged by both in vitro translation and fluorescence techniques. The tRNA$_f^{Ala}$(AAA) would not function for poly(U)-dependent elongation of polyalanine peptides while the corresponding tRNA$_f^{Ala}$(AAA) was efficiently used for this process. Conversely, both AcAla-tRNAs were capable of non-enzymatic binding to the P site of poly(U)-programmed 70S ribosomes in the presence of 15 mM Mg$^{2+}$. In this way, each could be used to begin polyalanine synthesis with tRNA$_f^{Ala}$(AAA) present as the elongator tRNA source. However, only the initiator tRNA analogue was enzymatically bound with IF-2 and GTP at 6 mM Mg$^{2+}$. The results indicate that tRNA$_f^{Ala}$(AAA) retains initiator function while only tRNA$_f^{Ala}$(AAA) can function for peptide elongation function.

The present invention is well adapted to carry out the objects and obtain the ends and advantages mentioned, as well as others inherent therein. While presently preferred embodiments of the invention have been described for the purpose of disclosure, numerous changes in the details of synthesis and use may be made without departing from the spirit of the present invention and the scope of the appended claims. It should be understood, therefore, that there is no intention to limit the invention to the specific form disclosed, but on the contrary, the invention is to cover all modifications, alternative constructions and equivalents falling within the spirit of the present invention and the scope of the appended claims.

What is claimed is:

1. A DNA sequence containing a synthetic tRNA, wherein said DNA sequence comprises:
    an AAA anticodon;
    a RNA polymerase promoter;

```
GAGAAGCTTT AATACGACTC ACTATAGGAG AGGTGTCCGA GTGGCTGAAG GAGCACGCCT

AAAAAGTGTG TATACGGCAA CGTATCGGGG GTTCGAATCC CCCCTCTCC GCCAGGATCC

GAGA
``` a tRNA gene, wherein said tRNA gene includes specific tRNA synthetase recognition sites for an amino acid of interest; and
    at least two restriction endonuclease sites.

2. DNA of claim 1, wherein said DNA includes a HindIII site, a T7 RNA polymerase promoter, a BstNI site, and a Bam HI site.

3. DNA of claim 2, further comprising a PstI site created by changing bases A21 and T24 to C21 and C24, respectively, and a SpeI site by adding an A between T42 and C43 in said tRNA gene.

4. DNA of claim 3, called tRNA$^{Cys}$(AAA) gene, having a nucleic acid sequence consisting of:

```
AGCTTTAATA CGACTCACTA TAGGCGCGTT AGCAAAGCGG TTCTGCAGCG GATTAAAAAT

CCGTACTAGT CCGGTTCGAC TCCGGAACGC GCCTCCAGGA TC
```

5. A method of preparing the tRNA$^{Cys}$(AAA) gene of claim 4 comprising:
    preparing 5'-3' and 3'-5' HindII/PstI oligomers and 5'-3' and 3'-5' PstI/BamHI oligomers;
    annealing said 5'-3' and 3'-5' HindIII/PstI oligomers and 5'-3' and 3'-5' PstI/BamHI oligomers;
    forming a ligation mixture of said annealed oligomers and a HindIII/BamHI-restricted pUC18 plasmid;
    incubating said ligation mixture;
    transforming E. coli with said incubated ligation mixture;
    exposing said transformed E. coli to ampicillin and X-gal;
    screening said transformed E. coli with plasmids containing ar insert for the presence of complete tRNA$^{Cys}$(AAA) genes; and
    sequencing both strands of said insert.

6. DNA of claim 2, further comprising a BstB1 restriction site within the T loop of said tRNA gene.

7. DNA of claim 6, called tRNA$^{Ser}$(AAA) gene, having a nucleic acid sequence consisting of:

8. A method of preparing the tRNA$^{Ser}$(AAA) gene of claim 7 comprising:
    copying the tRNA$^{Ser}$(GGA) gene from the E. coli genome;
    substituting AA for GG in said gene forming an AAA anticodon;
    blunting the ends of the ends of said substituted gene;
    restricting said blunt-ended gene with HindIII and BamHI;
    ligating said restricted gene into a pUC18 plasmid;
    transforming E. coli with said ligated plasmid;
    screening said transformed E. coli containing plasmids with an insert for the presence of complete tRNA$^{Ser}$(AAA) genes; and
    sequencing both strands of said insert.

9. DNA of claim 6, called tRNA$_e^{Ala}$(AAA) gene, having a nucleic acid sequence consisting of:

```
AGCTTTAATA CGACTCACTA TAGGGGCTAT AGCTCAGCTG GGAGAGCGCC TGCTTAAAAC

GCAGGAGGTC TGCGGTTCGA TCCCGCGTAG CTCCACCAGG ATCC
```

10. A method of preparing the tRNA$_e^{Ala}$(AAA) gene of claim 9 comprising:
    copying the tRNA$^{Ala}$(GGC) gene from the E. coli genome;
    substituting AAA for GGC in said gene forming an AAA anticodon;
    blunting the ends of said substituted gene;
    restricting said blunt-ended gene with HindIII and BamHI;
    ligating said restricted gene into a pUC18 plasmid;
    transforming E. coli with said ligated plasmid;

screening said transformed *E. coli* containing plasmids with an insert for the presence of complete tRNA$_e^{Ala}$(AAA) genes; and sequencing both strands of said insert.

11. DNA of claim 6, called tRNA$_f^{Ala}$(AAA) gene, having a nucleic acid sequence consisting of:

AGCTTTAATA CGACTCACTA TAGGGGGGGT GGAGCAGCCA TGGTAGCTCG TCGGGCTAAA

AACCCGAAGG TCGTCGGTTC AAATCCGGCC CCCTCTACCA GGATCC

12. A method of preparing the tRNA$_f^{Ala}$(AAA) gene of claim 11 comprising:
 copying the tRNA$_f^{Met}$(CAT) gene from the *E. coli* genome;
 substituting A's for bases C and T in the anticodon of said gene forming an AAA anticodon;
 substituting G's for bases 1C and 3C and T's for bases 70G and 72A of said substituted gene;
 inserting an A between bases 17C and 17aT of said substituted gene;
 blunting the ends of said substituted gene;
 restricting said blunt-ended gene with HindIII and BamHI;
 ligating said restricted gene into a pUC18 plasmid;
 transforming *E. coli* with said ligated plasmid;
 screening said transformed *E. coli* containing plasmids with an insert for the presence of complete tRNA$_f^{Ala}$(AAA) genes; and
 sequencing both strands of said insert.

* * * * *

UNITED STATES PATENT AND TRADEMARK OFFICE
CERTIFICATE OF CORRECTION

PATENT NO. : 5,358,862
DATED : October 25, 1994
INVENTOR(S) : Boyd Hardesty, et. al.

It is certified that error appears in the above-identified patent and that said Letters Patent is hereby corrected as shown below:

In Column 1, line 4, "division" should read --divisional--.

In Column 1, line 23, "ammo" should read --amino--.

In Column 1, line 65, "tRANs" should read --tRNAs--.

In Column 2, lines 47-48, "tRNA$^{Cys}$(-GCA)" should read --tRNA$^{Cys}$(GCA)--.

In Column 3, line 48, "(    )" should read --(••••)--.

In Column 3, line 48, "FIG. 4B in another" should read --FIG. 4B shows another--.

In Column 3, line 48, please insert the words --in which-- between the words "experiment" and "the".

In Column 3, line 54, "(-    -    )" should read --(-•• -••)--.

In Column 4, line 4, "protcolysis" should read --proteolysis--.

UNITED STATES PATENT AND TRADEMARK OFFICE
CERTIFICATE OF CORRECTION

Page 2 of 4

PATENT NO. : 5,358,862
DATED : October 25, 1994
INVENTOR(S) : Boyd Hardesty, et. al.

It is certified that error appears in the above-identified patent and that said Letters Patent is hereby corrected as shown below:

In Column 6, lines 51-52, please insert a comma between the words "ligating" and "transforming".

In Column 7, line 14, "BstNI (3) U/µg for" should read --BstNI (3 U/µg) for--.

In Column 8, line 36, "its" should read --it--.

In Column 9, lines 66-67, "AcSER-tRNA" should read --AcSer-tRNA--.

In Column 10 line 21, "[$^{4C}$]" should read --[$^{14}C$]--.

In Column 11, line 5, please insert the word --a-- between the words "which" and "nearly".

In Column 12, lines 41-42, "fiuorophore" should read --fluorophore--.

In Column 12, lines 44-45, please delete the words "we have".

In Column 12, line 49, "fiuorphore" should read --fluorophore--.

In Column 12, line 51, "fiuorophore" should read --fluorophore--.

In Column 13, line 32, "spectrofiuormeter" should read --spectrofluorometer--.

UNITED STATES PATENT AND TRADEMARK OFFICE
CERTIFICATE OF CORRECTION

PATENT NO. : 5,358,862

DATED : October 25, 1994

INVENTOR(S) : Boyd Hardesty, et. al.

It is certified that error appears in the above-identified patent and that said Letters Patent is hereby corrected as shown below:

In Columns 14 and 15, in the second line of the title for TABLE 3, "CPM − Ala−tRna$_i^{Ala/AAA}$" should read -- CPM − Ala−tRNA$_i^{Ala/AAA}$ --.

In Columns 14 and 15, the heading in TABLE 3 entitled "anistropy" should read --anisotropy--.

In Column 15, line 64, please remove the comma between the words "that" and "after".

In Column 16, line 31, "intiate" should read --initiate--.

In Column 16, under the heading "tRNA" of TABLE 4, "CPM-Ala-tRNA$_e$Ala/AAA" should read --CPM-Ala-tRNA$_e^{Ala/AAA}$--.

In Column 16, under the heading "addition" in TABLE 4, each occurrence of "+50S" and "+9 mM Mg$^{2+}$" should be indented under each occurrence of "+30S" and "+IF-2 & 30S".

In Column 16, in line 2 of the footnote of TABLE 4, "mg$^{2+}$" should read --Mg$^{2+}$--.

In Column 16, in line 3 of the footnote of TABLE 4, "and the 15" should read --and then 15--.

In Column 18, line 2, "is a inhibitor" should read --is an inhibitor--.

UNITED STATES PATENT AND TRADEMARK OFFICE
CERTIFICATE OF CORRECTION

PATENT NO. : 5,358,862
DATED : October 25, 1994
INVENTOR(S) : Boyd Hardesty, et. al.

It is certified that error appears in the above-identified patent and that said Letters Patent is hereby corrected as shown below:

In Column 18, line 4, please remove the comma after "effect".

In Column 21, lines 19-33, Claim 1 should read --DNA encoding a synthetic tRNA, comprising an RNA polymerase promoter, a mutant *E. coli* tRNA gene including an AAA anticodon and specific tRNA synthetase recognition sites for an amino acid other than Phe, and at least two restriction sites.--

In Column 21, line 67 (Claim 5), "ar" should read --an--.

Signed and Sealed this

Twenty-second Day of September, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: YES ( x i ) SEQUENCE DESCRIPTION: SEQ ID NO:1:

```
AGCTTTAATA CGACTCACTA TAGGCGCGTT AGCAAAGCGG TTCTGCAGCG GATTAAAAAT      60

CCGTACTAGT CCGGTTCGAC TCCGGAACGC GCCTCCAGGA TC                        102
```

( 2 ) INFORMATION FOR SEQ ID NO:2:

( i ) SEQUENCE CHARACTERISTICS:
        ( A ) LENGTH: 124 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: YES ( x i ) SEQUENCE DESCRIPTION: SEQ ID NO:2:

```
GAGAAGCTTT AATACGACTC ACTATAGGAG AGGTGTCCGA GTGGCTGAAG GAGCACGCCT      60

AAAAAGTGTG TATACGGCAA CGTATCGGGG GTTCGAATCC CCCCTCTCC GCCAGGATCC      120

GAGA                                                                  124
```

( 2 ) INFORMATION FOR SEQ ID NO:3:

( i ) SEQUENCE CHARACTERISTICS:
        ( A ) LENGTH: 104 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: YES ( x i ) SEQUENCE DESCRIPTION: SEQ ID NO:3:

```
AGCTTTAATA CGACTCACTA TAGGGGCTAT AGCTCAGCTG GGAGAGCGCC TGCTTAAAAC      60

GCAGGAGGTC TGCGGTTCGA TCCCGCGTAG CTCCACCAGG ATCC                      104
```

(2) INFORMATION FOR SEQ ID NO:4:

(i) SEQUENCE CHARACTERISTICS:
        (A) LENGTH: 106 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: YES (xi) SEQUENCE DESCRIPTION: SEQ ID NO:4:

```
AGCTTTAATA CGACTCACTA TAGGGGGGGT GGAGCAGCCA TGGTAGCTCG TCGGGCTAAA      60
AACCCGAAGG TCGTCGGTTC AAATCCGGCC CCCTCTACCA GGATCC                    106
```